United States Patent
Wunderlich et al.

(10) Patent No.: US 9,243,714 B2
(45) Date of Patent: Jan. 26, 2016

(54) SEALING SYSTEM AND RETRACTABLE ASSEMBLY INCLUDING SUCH

(71) Applicant: Endress +Hauser Conducta Gesellschaft für Mess- und Regeltechnik mbH + Co. KG, Gerlingen (DE)

(72) Inventors: Ingrid Wunderlich, Radebeul (DE); Thomas Pfauch, Leipzig (DE)

(73) Assignee: Endress + Hauser Conducta Gesellschaft für Mess- und Regeltechnik mbH + Co. KG, Gerlingen (DE)

( * ) Notice: Subject to any disclaimer, the term of this patent is extended or adjusted under 35 U.S.C. 154(b) by 0 days.

(21) Appl. No.: 14/506,834

(22) Filed: Oct. 6, 2014

(65) Prior Publication Data
US 2015/0097343 A1  Apr. 9, 2015

(30) Foreign Application Priority Data
Oct. 7, 2013 (DE) .......................... 10 2013 111 057

(51) Int. Cl.
*F16K 3/24* (2006.01)
*F16J 15/18* (2006.01)
*F16J 15/32* (2006.01)
*F16K 11/07* (2006.01)
*G01N 1/20* (2006.01)

(52) U.S. Cl.
CPC ................ *F16J 15/18* (2013.01); *F16J 15/184* (2013.01); *F16J 15/3276* (2013.01); *F16K 11/0712* (2013.01); *G01N 1/2035* (2013.01)

(58) Field of Classification Search
CPC .............. F16J 15/16; F16J 15/18; F16J 15/26
See application file for complete search history.

(56) References Cited

U.S. PATENT DOCUMENTS

| 3,990,711 | A | | 11/1976 | Hill |
| 4,371,178 | A | | 2/1983 | Ott |
| 4,776,599 | A | * | 10/1988 | Vezirian .................... 175/371 |
| 5,263,682 | A | * | 11/1993 | Covert et al. .............. 251/214 |
| 7,055,390 | B2 | * | 6/2006 | Foote et al. .................. 73/700 |
| 8,186,202 | B2 | * | 5/2012 | Lafleur et al. ................. 73/37 |

(Continued)

FOREIGN PATENT DOCUMENTS

| BE | 694996 | | 8/1967 |
| DE | 278461 | | 2/1970 |
| DE | 30027715 | A1 | 7/1981 |

(Continued)

OTHER PUBLICATIONS

German Search Report, German PTO, Munich, Feb. 24, 2014.

*Primary Examiner* — Gilbert Lee
(74) *Attorney, Agent, or Firm* — Bacon & Thomas, PLLC

(57) ABSTRACT

A retractable assembly and a sealing system, the sealing system comprising: an essentially hollow, cylindrical housing with an inner space and a peripheral groove open to the inner space in the housing. The peripheral groove defines a plane in the housing and the normal of the plane is parallel to the longitudinal axis of the housing. The groove includes at least one, preferably two, extension spaces expanding the groove. The extension space is arranged on the side of the groove facing away from the inner space. An annular seal corresponding to the groove is arranged in the groove. The annular seal is formed of at least a first section facing the inner space and a second section facing away from the inner space.

11 Claims, 3 Drawing Sheets

(56) References Cited

U.S. PATENT DOCUMENTS

| | | |
|---|---|---|
| 2012/0272756 A1 | 11/2012 | Pfauch |
| 2013/0036843 A1 | 2/2013 | Pfauch |

FOREIGN PATENT DOCUMENTS

| | | |
|---|---|---|
| DE | 4110164 A1 | 10/1992 |
| DE | 102006022979 A1 | 11/2007 |
| DE | 102006022983 A1 | 11/2007 |
| DE | 102006040052 A1 | 3/2008 |
| DE | 102006048898 A1 | 4/2008 |
| DE | 102009020440 A1 | 12/2010 |
| DE | 102009048787 A1 | 4/2011 |
| DE | 102011017535 A1 | 10/2012 |
| DE | 102011080579 A1 | 2/2013 |
| DE | 102012206675 A1 | 10/2013 |
| EP | 0305252 A1 | 3/1989 |
| EP | 2019312 A2 | 1/2009 |
| EP | 2251650 A3 | 11/2010 |
| EP | 2366934 A1 | 9/2011 |
| WO | 2013160267 A1 | 10/2013 |

* cited by examiner

SEALING SYSTEM AND RETRACTABLE ASSEMBLY INCLUDING SUCH

TECHNICAL FIELD

The invention relates to a sealing system and to a retractable assembly including such a sealing system.

BACKGROUND DISCUSSION

Retractable assemblies are manufactured and sold by the group of firms, Endress+Hauser, in a large multiplicity of variants, an example being "Cleanfit H CPA475".

Retractable assemblies are widely used in analytical measurements technology and process automation. They serve to withdraw probes from the process, and therewith from the medium, without process interruption and then to reintroduce them back into the process. The probes are held in an immersion tube and moved by means of a drive manually or automatically, for example pneumatically, axially between a process position (measuring) and a service position (maintenance, calibrating, rinsing, washing, probe replacement, etc.). These procedures occur periodically or as a function of other determinable or measured parameters.

Probes in the sense of this invention comprise probes with at least one receptacle for at least one sensor for measuring one or more physical or chemical, process variables.

The fields of use of retractable assemblies for measuring physical or chemical, process variables of a medium, e.g. of a fluid, especially a liquid, in process technology are many. The sensors are used for determining the process variables. The sensors can be, for example, pH-sensors, conductivity sensors, optical or electrochemical sensors for determining a concentration of a substance, e.g. $O_2$, $CO_2$, certain ion types, organic compounds, or the like, contained in the medium to be monitored.

If retractable assemblies are used for holding the sensor for determining at least one process variable, the sensor can in the service position be checked, calibrated, cleaned and/or replaced, wherein the sensor is, in such case, located in the housing interior of the retractable assembly, in the so-called service chamber. In order that the medium not be contaminated by the calibration-, rinse/wash- or cleaning liquid, in the service position the service chamber is so sealed relative to the containment, in which the medium is located, that no exchange of medium/liquid can take place. Usually, there is located for this purpose on the media end of the housing of the retractable assembly a seal, which in interaction with the end region of the immersion tube prevents an exchange of medium/liquid. This seal is located on the immersion tube or in the housing (service chamber). The seal is often embodied as an O-ring. The groove for the seal is, in such case, rectangularly shaped in cross section. In interaction with the circularly shaped O-ring, gaps result.

The gaps and edges form dead spaces, where then particles can easily deposit and scale and/or biofilms can form. These are undesirable, since then the performance of the retractable assembly suffers. In the worst case, germs and the like collect, multiply and so contaminate the medium and therewith render it unusable.

SUMMARY OF THE INVENTION

An object of the invention is to provide a sealing system and a retractable assembly, which satisfy hygienic requirements.

The object is achieved by a sealing system, comprising: An essentially hollow, cylindrical housing with an inner space and a peripheral groove open to the inner space in the housing, wherein the peripheral groove defines a plane in the housing and the normal of the plane is parallel to the longitudinal axis of the housing, wherein the groove includes at least one, preferably two, extension spaces expanding the groove, wherein the extension space is arranged on the side of the groove facing away from the inner space; an annular seal corresponding to the groove and arranged in the groove, wherein the annular seal is formed of at least a first section facing the inner space and a second section facing away from the inner space, wherein the first section includes a dynamic sealing surface; and a component, which is movable parallel to the longitudinal axis of the housing and which has an end region, wherein the component is so embodied that in a first position it closes and gap-freely seals the inner space of the housing, especially when the end region of the movable component is located at the same axial position as the annular seal, especially the same axial position as the dynamic sealing surface.

In this way, that at the transitional region of inner space to external space, a gap-free seal between annular seal and end region of the movable component arises, hygienic requirements can be fulfilled.

In a preferred embodiment, the housing includes a first part and a second part, wherein the first part makes the housing connectable with a containment, wherein the second part forms the inner space, wherein the groove is formed by the assembly of the first part with the second part, and wherein the second section includes a first static sealing surface and a second static sealing surface, wherein the annular seal is so embodied that the groove surrounds the annular seal at least at the first static sealing surface and the second static sealing surface gap-freely.

The two-part construction facilitates manufacturing and installation of the annular seal occurs simply. Additionally, the two additional, gap-free, sealing surfaces assure that hygienic requirements can be fulfilled.

In a preferred embodiment, the cross section of the annular seal is formed from the combination of a circularly shaped section facing away from the inner space, and a rectangularly shaped section facing the inner space. Other embodiments are possible. The described embodiment permits fulfillment of the posed requirements.

Advantageously, the cross section of the groove is smaller than the cross section of the annular seal. Thus, the annular seal is slightly compressed and some pressure is exerted inwardly. Especially, the circular section is smaller than the groove. In this way, the upper and lower parts of the circularly shaped section are compressed upwardly, respectively downwardly.

The terms "above", "upwards" and related terms mean in the sense of this invention away from the medium, while "below", "beneath" and related terms mean in the sense of this invention toward the medium. "Outside", "outwards" and related terms mean in the sense of this invention away from the longitudinal axis of the housing, while "inner", "within" and related terms mean in the sense of this invention toward the longitudinal axis.

In an advantageous form of embodiment, the material of the annular seal is ethylene-propylene rubber (EPM), ethylene-propylene-diene rubber (EPDM), a fluorine containing rubber (FKM), perfluoro rubber (FFKM), polytetrafluoroethylene (PTFE) or a silicone.

Preferably, the volume of the extension space corresponds to 3-20% of the volume of the annular seal. Through the application at least of one extension space, an option is that the annular seal can expand as temperature changes, especially a temperature rise, into the extension space, and, thus, also at changed temperatures a gap-free seal is assured at the dynamic and first, respectively second static sealing surfaces.

The object is further achieved by a retractable assembly for measuring at least one measured variable of a medium in a containment, comprising an essentially hollow, cylindrical housing having a service chamber formed in the inner space of the housing; an immersion tube having an end region, which is axially movable in the housing between a service position run out from the medium and a process position run into the medium, wherein in the service position the immersion tube is positioned in the service chamber; at least one sealing system such as above described, wherein the housing is formed by the retractable assembly housing, wherein the movable component is formed by the immersion tube, wherein the first position corresponds to the service position, wherein in the service position the annular seal closes and gap-freely seals off the service chamber, in that the end region of the immersion tube lies against the dynamic sealing surface of the annular seal.

In an advantageous variant, a rinsing/washing chamber is provided, which is arranged in the housing between the containment and the service chamber, wherein a sealing system such as above described seals the service chamber from the rinsing/washing chamber.

With addition of the service chamber, thus, two different chambers are available for performing work on the probe. Exactly in the case of hygienic applications, the rinsing/washing chamber can then be used as an additional barrier between medium and service chamber.

In a preferred embodiment, there is arranged on the housing for the service chamber and/or for the rinsing/washing chamber at least one rinse, wash connection, which is so embodied that washing, or rinsing, medium flowing through the rinse, wash connection rinses, washes, cleans and/or sterilizes the annular seal, especially the dynamic sealing surface, when the end region of the immersion tube, in the case of movement from the service position into the process position, runs over the annular seal.

In this regard, the immersion tube includes on its end facing the medium a cage-like opening, in which the sensor is located. Alternatively or supplementally, the immersion tube can flare upwardly.

For performing the cleaning procedure, preferably a locking apparatus is provided, which locks the immersion tube in a position, in which a cleaning of the annular seal is possible. Preferably in this position, the already mentioned rinsing/cleaning/sterilization of the dynamic sealing surface is performed.

BRIEF DESCRIPTION OF THE DRAWINGS

The invention will now be explained based on the appended drawing, the figures of which show as follows.

DETAILED DISCUSSION IN CONJUNCTION WITH THE DRAWINGS

Figure 1:
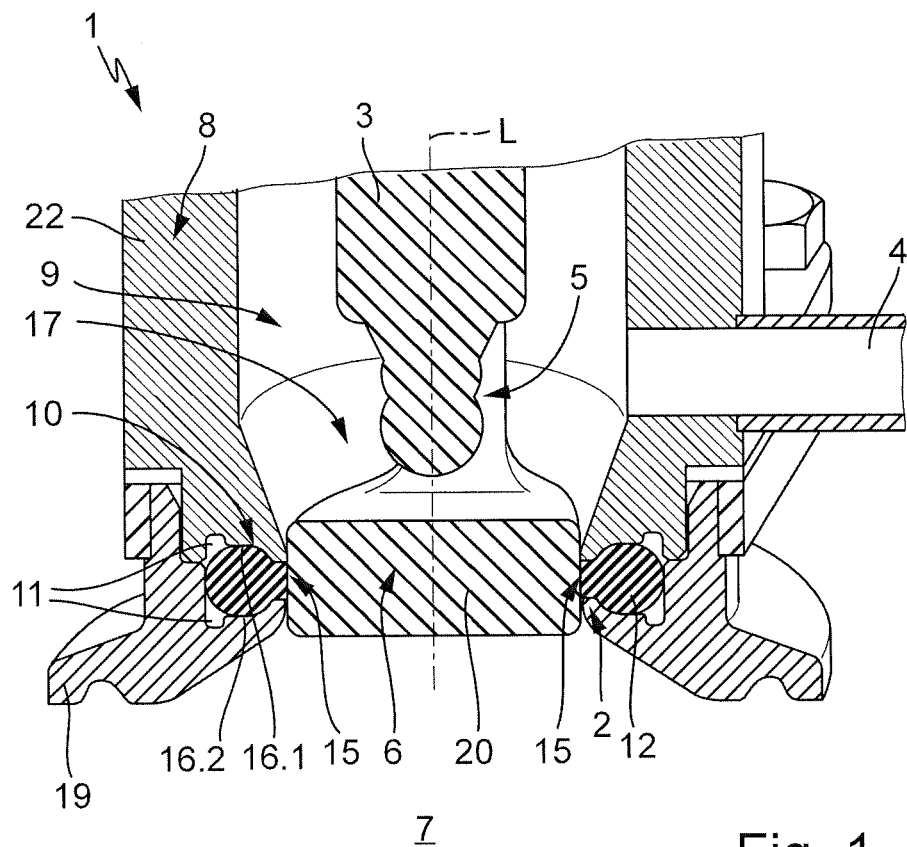
FIG. 1 is a retractable assembly of the invention with installed sealing system of the invention.

In the figures, equal features are provided with equal reference characters.

Figure 3:
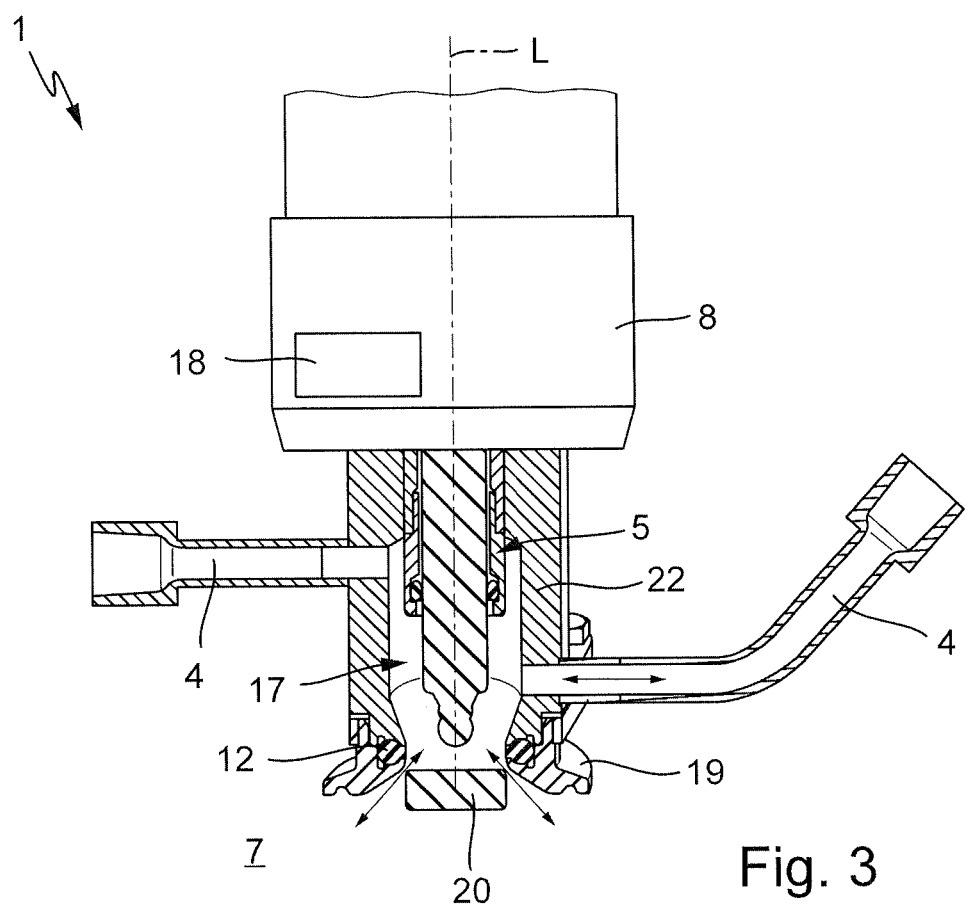
FIG. 3 is a retractable assembly of the invention with installed sealing system of the invention in a position for rinsing/washing the sealing system.

The retractable assembly of the invention bears the reference character 1 and is shown in FIGS. 1 and 3. The retractable assembly 1 is composed of an essentially cylindrical, retractable assembly housing 8, which can be connected by means of a process connection 19 to a containment (not shown). The process connection 19 can be, for instance, a flange connection, made e.g. of stainless steel. The process connection 19 will be explored in greater detail later. Located in the containment is the medium 7 to be measured. The containment can be, for instance, a container, kettle, tube, pipeline and the like.

The terms "above", "upwards" and related terms mean in the sense of this invention away from the medium 7, while "below", "beneath" and related terms mean in the sense of this invention toward the medium. "Outside", "outwards" and related terms mean in the sense of this invention away from the longitudinal axis L of the housing 8, while "inner", "within" and related terms mean in the sense of this invention toward the longitudinal axis L.

FIG. 1 shows the retractable assembly 1 in the service position. This is explained in greater detail in the following.

Guided within the housing 8 is an immersion tube 5. A probe is connected with the immersion tube 5, for example, by a screwed connection, i.e. the probe is mounted in the immersion tube 5. The probe in the sense of this invention includes probes having at least one receptacle for at least one sensor 3 for measuring one or more physical or chemical, process variables. Such include, for example, pH-value, also via an ISFET, redox-potential, absorption of electromagnetic waves in the medium, for example, with wavelengths in the UV-, IR-, and/or visible region, oxygen content, conductivity, turbidity, concentration of metal and/or non-metal substances and temperature.

If the immersion tube 5 is located in the service position, a portion of the immersion tube 5, especially the sensor 3, is located in the inner space 9, in the so-called service chamber 17, for rinsing, washing, cleaning, calibrating etc. Located at the lower end region 6 (thus toward the medium) of the immersion tube 5 is a closure element 20 for sealing from the process. The closure element 20 seals the inner space 9 from the process, and therewith from the medium 7. The medium 7 can be hot, poisonous, corrosive or in other manner damaging for humans and the environment. It is, consequently, to be heeded that the closure element 20 seals safely and durably. For such purpose, a sealing system 2 is provided on the/in the housing 8, especially one or more formed seals 12 are used. This will be further explained below in greater detail.

In the service position, the most varied of service tasks can be performed, such as cleaning or calibration. Through a connection 4, in such case, cleaning-, rinse-, wash- and calibration liquid can be brought into the inner space 9. Through a corresponding, additional outlet, the liquid can, in turn, be drained out (see in this regard, for instance, the upper connection 4 in FIG. 3, wherein the retractable assembly 1 is installed inclined relative to vertical; it is to be noted that the rinse, wash direction can also be reversed).

Immersion tube 5 can be produced from different materials. The state of the art contains immersion tubes 5 of stainless steel, titanium and other chemically resistant materials. The immersion tube 5 can also be produced from a synthetic material such as polyetheretherketone (PEEK), polytetrafluoroethylene (PTFA), a perfluoroalkoxy polymer (PFA), or some other synthetic material or resistant metals, such as, for instance, Hastelloy. The same holds for housing 8.

Immersion tube 5 is axially displaceably guided for movement toward the medium 7, respectively in the direction away from the medium 7, along the central axis L. Immersion tube 5 is, in such case, moved between the service position run into the housing 8 (such as described, see FIG. 1) and the process position run out from the housing 2, i.e. the sensor 3 is in this position in contact with the medium 7.

The shifting of the immersion tube 5 is effected by a manual or automatic drive, for instance, by means of an energy supply (not shown in greater detail). If the energy supply is brought about by a connection (not shown), the immersion tube 5 moves from the service—into the process position. A further connection (likewise not shown) serves then as drain. If the energy supply is introduced in the reverse direction, the immersion tube 5 moves from the process—into the service position. Known from the state of the art are pneumatic, hydraulic and electrical drives.

Measuring takes place in the process position. The probe, respectively the sensor 3, has access to the medium 7 to be measured via a cage-like opening in the immersion tube 5. Alternatively or supplementally, the immersion tube flares upwardly (thus away from the medium), in order to enable rinsing, washing, cleaning and sterilizing of the immersion tube 5, especially of the closure element 20, (see details in the description of FIG. 3)

In the following, the sealing system 2 for sealing inner space 9 from the containment, respectively medium 7, will now be described in greater detail.

The sealing system 2 is essentially formed of three parts: an annular seal 12, a groove 10 for the annular seal 12 in the housing 8 and the closure element 20 in the end region 6 of the immersion tube 5, thus the movable part of the retractable assembly 1.

Housing 8 is formed by a process connection 19 and a second part 22. Groove 10 is formed by corresponding cavities in the process connection 19 and in the second part 22 of the housing 8. Groove 10 defines a plane, wherein the normal to the plane extends essentially parallel to the longitudinal axis of the housing 8. Through the assembly (for instance, by screwed connection) of the process connection 19 with the second part 22, there arises in the housing 8 the encircling groove 10 open to the inner space 9. Also, a replacement of the annular seal 12 can occur by disassembling the process connection 19 and the second part 22 of the housing 8. The two-part construction of the housing 8 facilitates manufacturing, and installation of the annular seal occurs simply. Also, the groove 10 can be produced with the required accuracy, especially surface roughness.

Figure 2:
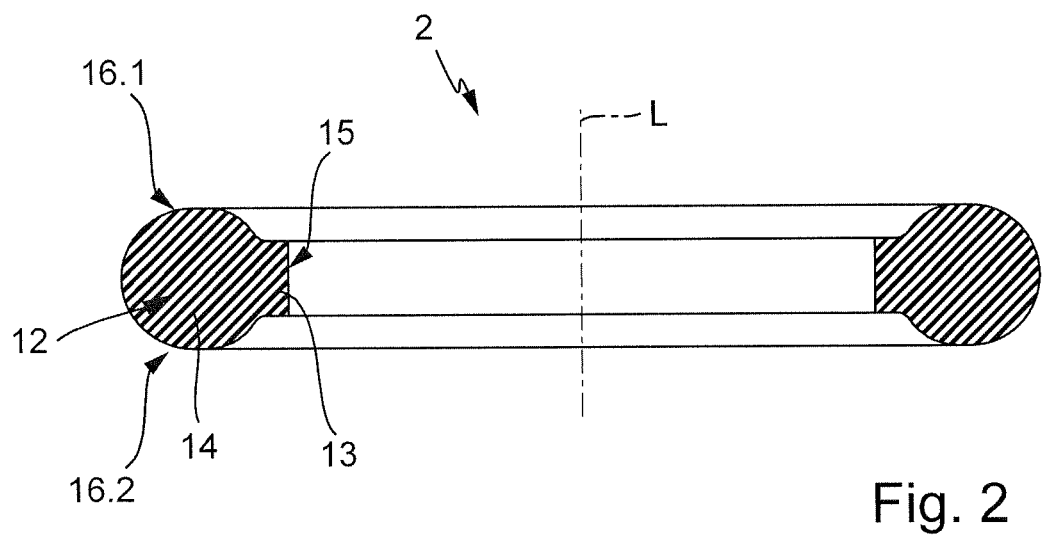
FIG. 2 is a sealing system of the invention in an enlarged representation.

The annular seal 12 for the groove 10 is shown in greater detail in FIG. 2. Annular seal 12 includes a first section 13 facing the inner space 9 and a second section 14 facing away from the inner space 9. In the example, the first section 13 is rectangular in cross section and the second section 14 circular in cross section. The first section 13 and the second section 14 form a step at their junction. The most varied of forms, such as, for instance, a wedge shape, provide other options.

The groove 10 and the annular seal 12 are so embodied that a dynamic sealing surface 15 is formed. The dynamic sealing surface 15 is an internally situated, encompassing area of the annular seal 12. The dynamic sealing surface 15 is essentially flush with an inner edge of the housing 8.

The inner space 9 is gap-freely sealed from the containment, respectively the medium 7, especially by the dynamic sealing surface 15 in interaction with the immersion tube 5, more exactly the closure element 20. Thus, no gap can form between housing 8 and annular seal 12. In an embodiment, the dynamic sealing surface 15 protrudes into the inner space 9; this region is in the case of movement of the immersion tube 5 over the annular seal 12 first slightly outwardly pressed.

Additionally, the groove 10 is so embodied that in the second section 14 at least a first static sealing surface 16.1 and another, second static sealing surface 16.2 are formed. The first static sealing surface 16.1 is arranged above the annular seal 12 on the second section 14, while the second static sealing surface 16.2 is arranged below the second section 14 on the annular seal 12. The first and second static sealing surface 16.1, 16.2 seal the inner space 9 gap-freely from the external space. Additionally, the first and second static sealing surfaces 16.1, 16.2 are responsible for assuring that the process connection 19 and the second part 22 of the housing 8 are sealed relative to one another.

There are, thus, as a whole, at least three gap-free sealing surfaces. In order to assure this gap freedom further, the cross section of the groove 10 is embodied to be smaller than the cross section of the annular seal 12.

The annular seal 12 is composed, for example, of ethylene-propylene rubber (EPM), ethylene-propylene-diene rubber (EPDM), a fluorine containing rubber (FKM), perfluoro rubber (FFKM), polytetrafluoroethylene (PTFE) or a silicone.

Located at the outer part of the groove 10 is an extension space 11 expanding the groove 10. Preferably, as shown in the example, there are two extension spaces 11. The volume of the extension spaces 11 amounts typically to 5-15% of the volume of the annular seal 12. The area of the annular seal 12 lying opposite the dynamic sealing surface 15 adjoins the extension spaces 11.

In the case of temperature change, for example, brought about by a sterilization procedure, the annular seal 12 can expand into the extension spaces 11 without that gap freedom at the dynamic, first and second static sealing surfaces 15, 16.1, 16.2 is degraded. In other words, gaps do not form at any temperature. Depending on material, the annular seal 12 can experience temperature changes of −20° C. to +140° C.

For hygienic purposes, it is necessary to clean, i.e. to rinse, wash, clean and, when required, sterilize the annular seal 12. FIG. 3 illustrates this cleaning procedure. The immersion tube 5 runs into a position, which is located between the service position and the process position. This is locked by a locking apparatus 18. The locking apparatus 18 is symbolically presented in FIG. 3 and is, for instance, a locking element, self-limiting drive or automatically operating mechanism.

Rinse-, cleaning- or sterilization medium inflowing through the lower connection 4 flows around the annular seal 12 and thus rinses, cleans or sterilizes it. The inflowing medium can drain into the medium 7 (whose flow is, when required, turned off), respectively into the containment.

Figure 4:
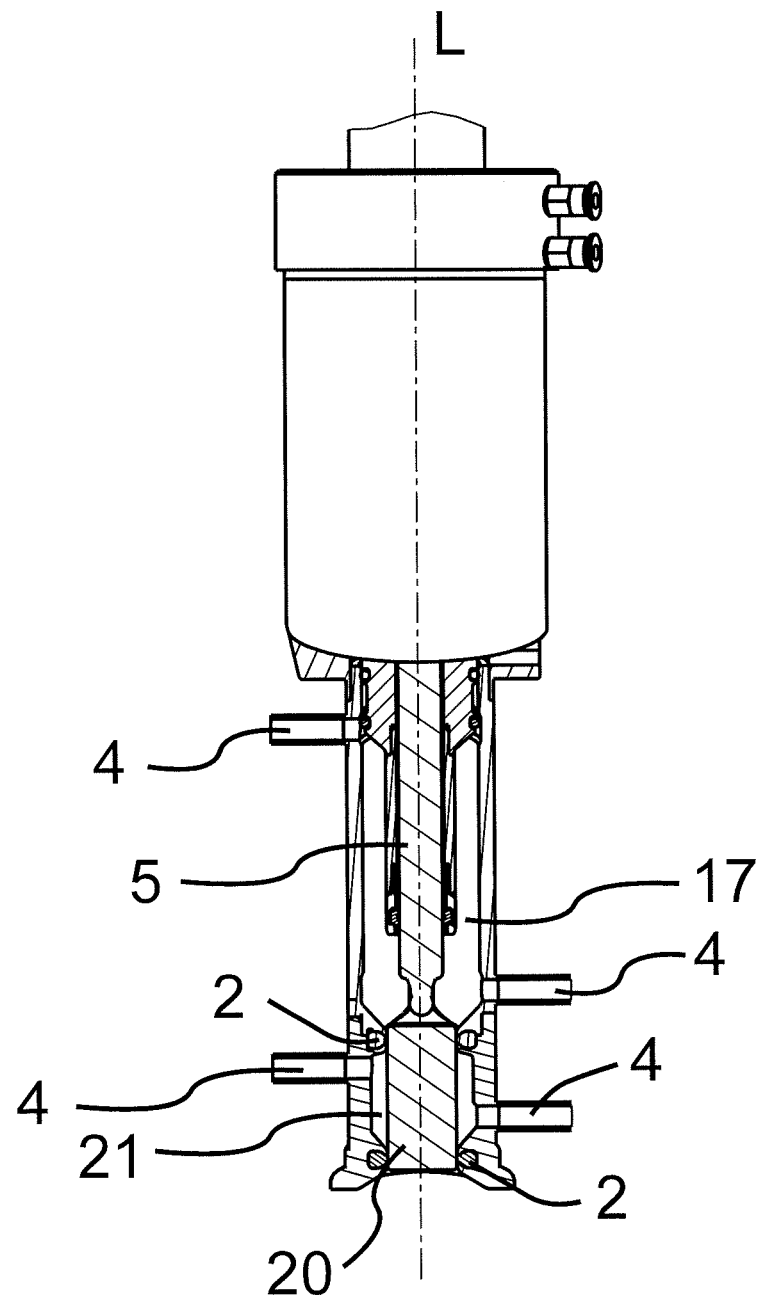
FIG. 4 is a retractable assembly of the invention with an additional rinsing/washing chamber.

In an embodiment, there is located in FIG. 4 in the housing 8 below the service chamber 17, thus between the service chamber 17 and the containment, another chamber, the so called rinsing/washing chamber 21. Exactly in the case of hygienic applications, this chamber 21 can be utilized as an additional barrier between medium 7 and service chamber 17. Counting the service chamber 17, there are then two different chambers available for performing work on the probe. An example of this is sterilization or calibration of the probe in the service chamber 17. Other rinse, wash connections 4 can be present. Service chamber 17 and rinsing/washing chamber 21 are likewise sealed relative to one another by a sealing system of the invention.

The invention claimed is:

1. A sealing system, comprising:
an essentially hollow, cylindrical housing with an inner space and a peripheral groove open to the inner space in said housing, said peripheral groove defines a plane in said housing and the normal of the plane is parallel to the longitudinal axis of said housing, said groove includes at least one, extension space expanding said groove, and said extension space is arranged on the side of said groove facing away from said inner space;
an annular seal corresponding to said groove and arranged in said groove, said annular seal is formed of at least a first section facing said inner space and a second section facing away from said inner space; and
wherein a component, which is movable parallel to the longitudinal axis of said housing and which has an end region, which is so embodied that in a first position it closes and gap-freely seals said inner space of said housing, especially when said end region of said movable component is located at the same axial position as said annular seal, especially the same axial position as a dynamic sealing surface, wherein:
the first section includes said dynamic sealing surface.

2. The sealing system as claimed in claim 1, wherein:
said housing includes a first part and a second part;
said first part makes said housing connectable with a containment;
said second part forms said inner space;
said groove is formed by the assembly of said first part with said second part; and
said second section includes a first static sealing surface and a second static sealing surface; and
said annular seal is so embodied that said groove surrounds said annular seal at least at said first static sealing surface and said second static sealing surface gap-freely.

3. The sealing system as claimed in claim 1, wherein:
the cross section of said annular seal is formed from the combination of a circularly shaped section facing away from said inner space, and a rectangularly shaped section facing said inner space.

4. The sealing system as claimed in claim 1, wherein:
the cross section of said groove is smaller than the cross section of said annular seal.

5. The sealing system as claimed in claim 1, wherein:
the material of said annular seal is ethylene-propylene rubber (EPM), ethylene-propylene-diene rubber (EPDM), a fluorine containing rubber (FKM), perfluoro rubber (FFKM), polytetra-fluoroethylene (PTFE) or a silicone.

6. The sealing system as claimed in claim 1, wherein:
the volume of said extension space is 3-15% of the volume of said annular seal.

7. The retractable assembly as claimed in claim 1, wherein said groove includes two extension spaces expanding said groove, and said extension spaces are arranged on the side of said groove facing away from said inner space.

8. A retractable assembly for immersion-, flow- and attachment measuring systems in analytical process technology for measuring at least one measured variable of a medium in a containment, comprising:
an essentially hollow, cylindrical, housing having a service chamber formed in the inner space of said housing; and
an immersion tube having an end region, which is axially movable in said housing between a service position run out from the medium and a process position run into the medium; wherein:
in the service position said immersion tube is positioned in said service chamber;
at least one sealing system as claimed in claim 1;
said housing is formed by the retractable assembly housing;
said movable component is formed by said immersion tube;
the first position corresponds to the service position; and
in the service position said annular seal closes and gap-freely seals off said service chamber, in that said end region of said immersion tube lies against said dynamic sealing surface of said annular seal.

9. The retractable assembly as claimed in claim 8, further comprising:
a rinsing/washing chamber, which is arranged in said housing between containment and said service chamber, wherein:
a sealing system as claimed in claim 1 seals said service chamber from said rinsing/washing chamber.

10. The retractable assembly as claimed in claim 8, wherein:
arranged on said housing for said service chamber and/or for said rinsing/washing chamber is at least one rinse, wash connection, which is so embodied that washing, or rinsing, medium flowing through said rinse, wash connection rinses, washes, cleans and/or sterilizes said annular seal or seals, especially said dynamic sealing surface, when said end region of said immersion tube in the case of the movement from the service position into process position runs over said annular seal.

11. The retractable assembly as claimed in claim 10, further comprising:
a locking apparatus, which locks said immersion tube in a position, in which a cleaning of said annular seal is possible.

* * * * *